US009913850B2

(12) United States Patent
New et al.

(10) Patent No.: US 9,913,850 B2
(45) Date of Patent: Mar. 13, 2018

(54) BILE ACIDS AND BIGUANIDES AS PROTEASE INHIBITORS FOR PRESERVING THE INTEGRITY OF PEPTIDES IN THE GUT

(75) Inventors: Roger R. C. New, London (GB); Glen Travers, London (GB)

(73) Assignee: AXCESS LIMITED, London (GB)

( * ) Notice: Subject to any disclaimer, the term of this patent is extended or adjusted under 35 U.S.C. 154(b) by 636 days.

(21) Appl. No.: 13/122,241

(22) PCT Filed: Oct. 1, 2009

(86) PCT No.: PCT/AU2009/001305
§ 371 (c)(1),
(2), (4) Date: Oct. 25, 2011

(87) PCT Pub. No.: WO2010/037173
PCT Pub. Date: Apr. 8, 2010

(65) Prior Publication Data
US 2012/0035116 A1 Feb. 9, 2012

(30) Foreign Application Priority Data

Oct. 1, 2008 (GB) .................................. 0817969.9

(51) Int. Cl.
| A61K 38/12 | (2006.01) |
| A61K 31/575 | (2006.01) |
| A61K 31/155 | (2006.01) |
| A61K 45/06 | (2006.01) |
| A61K 9/20 | (2006.01) |
| A61K 9/28 | (2006.01) |

(52) U.S. Cl.
CPC .......... *A61K 31/575* (2013.01); *A61K 31/155* (2013.01); *A61K 38/12* (2013.01); *A61K 45/06* (2013.01); *A61K 9/2013* (2013.01); *A61K 9/28* (2013.01)

(58) Field of Classification Search
CPC .............. A61K 2300/00; A61K 31/155; A61K 31/575; A61K 38/12; A61K 45/06; A61K 9/2013; A61K 9/28
See application file for complete search history.

(56) References Cited

U.S. PATENT DOCUMENTS

| 4,579,730 | A * | 4/1986 | Kidron et al. ................. 424/465 |
| 5,085,864 | A * | 2/1992 | Cannon .................. A61K 31/70 424/422 |
| 5,534,505 | A * | 7/1996 | Widauer .............. A61K 31/575 514/169 |
| 5,853,748 | A | 12/1998 | New |
| 6,156,731 | A | 12/2000 | Grass et al. |
| 8,242,294 | B2 * | 8/2012 | Moriarty .............. A61K 31/575 552/549 |
| 8,314,058 | B2 * | 11/2012 | New ........................ A61K 9/19 514/1.1 |
| 2003/0124061 | A1 * | 7/2003 | Roberts ........................ 424/10.1 |
| 2006/0122097 | A1 | 6/2006 | New |
| 2006/0247171 | A1 * | 11/2006 | Kirk ................................ 514/12 |
| 2007/0265187 | A1 * | 11/2007 | Vukicevic .......... A61K 38/1875 514/8.8 |
| 2009/0041849 | A1 | 2/2009 | New |
| 2009/0175841 | A1 | 7/2009 | Berry et al. |
| 2010/0048454 | A1 | 2/2010 | Arbit et al. |

FOREIGN PATENT DOCUMENTS

| EP | 0 462 071 A1 | 12/1991 |
| WO | WO 96/06635 A1 | 3/1996 |
| WO | WO 97/21448 A1 | 6/1997 |
| WO | 2001/009163 | 2/2001 |
| WO | 2004/091667 | 10/2004 |
| WO | WO 2005/110465 A2 | 11/2005 |
| WO | WO 2006/017541 A2 | 2/2006 |
| WO | WO 2006/127948 A2 | 11/2006 |
| WO | WO 2007/029238 A2 | 3/2007 |
| WO | WO 2007/032013 A2 | 3/2007 |
| WO | 2007/093806 | 8/2007 |

OTHER PUBLICATIONS

Weissberg et al. The Value of a Special Pepsin-Pancreatic Preparation in the Treatment of Peptic Ulcer and Gastric Hyperacidity. Oct. 1948. vol. 15, No. 10, pp. 332-336.*
Bjorkhem et al. Assay of the major bile acids in serum by isotope dilution-mass spectrometry. Scand J Clin Lab Invest 1983, vol. 43. pp. 163-170.*
Betaine Hydrochloride (HCL) with Pepsin. Accessed online at http://www.modernherbalist.com/betaine.html on Aug. 31, 2016. 4 pages.*
International Search Report for PCT/AU2009/001305, dated Nov. 26, 2009.
Wen et al., "Enzymatic Degradation of Luteinizing Hormone Releasing Hormone (LHRH) by Mucosal Homogenates form the Intestine of the Common Brushtail Possum (*Trichosurus vulpecular*)" Life Sci. (2002) vol. 71, pp. 3019-3030.
Ledger et al., "The Metabolic Barrier of the Lower Intestinal Tract of Salmon to the Oral Delivery of Protein and Peptide Drugs", J. Control. Release (2002) vol. 83, pp. 91-103.
Yamamoto et al., "Effects of Various Protease Inhibitors on the Intestinal Absorption and Degradation of Insulin in Rats", Pharm. Res. (1994) vol. 11, No. 10, pp. 1496-1500.
Uchiyama et al., "Effects of Various Protease Inhibitors on the Stability and Permeability of [D-Ala$^2$, D-Leu5]enkephalin in the Rat Intestine: Comparison with Leucine Enkephalin" J. Pharm., Sci. (1988) vol. 87. No. 4, pp. 448-452.
Okagawa et al., "Susceptibility of Eberatide to Proteolysis in Rat Intestinal Fluid and Homogenates and its Protection by Various Protease Inhibitors", Life Sci. (1994) vol. 55, No. 9, pp. 677-683.
International Preliminary Report on Patentability for PCT/AU2009/001305, dated Jul. 30, 2010.

(Continued)

*Primary Examiner* — Marcela M Cordero Garcia
(74) *Attorney, Agent, or Firm* — Nixon & Vanderhye P.C.

(57) ABSTRACT

This invention relates to methods of preserving the integrity of peptides in the gut. In particular it concerns the use of certain compounds as inhibitors of gut proteases. Compounds identified as having gut protease inhibitory activity are biguanides, certain bile acids and pharmaceutically acceptable salts of these compounds. This activity makes these compounds useful for co-administration with prophylactic or therapeutic peptides. This invention relates to methods of inhibiting gut proteases and peptide formulations comprising these gut protease inhibitor.

6 Claims, 16 Drawing Sheets

(56) References Cited

OTHER PUBLICATIONS

Written Opinion for PCT/AU2009/001305, dated Nov. 26, 2009.
Extended European Search Report in EP 09 81 7101 dated Apr. 23, 2012.
Eto et al, "Inhibition of pepsin activity by ursodeoxycholic . . . ", American Journal of Surgery, Paul Hoeber, NY, NY, vol. 150, No. 5, Nov. 1, 198, pp. 564-567, XP023227697.
Thorne et al, "Effect of Zinc on the proteolytic . . . ", vol. 40, No. 5, 1991, pp. 612-620; XP008150752.
Greiner, "Reduction of proteolytic degradation . . . ", Journal of Dental Research Mar. 1993 LNKD-PUBMED:8383711, vol. 72, No. 3, Mar. 1993, pp. 630-633, XP008150750.

* cited by examiner

BILE ACIDS AND BIGUANIDES AS PROTEASE INHIBITORS FOR PRESERVING THE INTEGRITY OF PEPTIDES IN THE GUT

This application is the U.S. national phase of International Application No. PCT/AU2009/001305 filed 1 Oct. 2009, which designated the U.S. and claims priority to Great Britain application no. 0817969.9 filed 1 Oct. 2008, the entire contents of each of which are hereby incorporated by reference.

FIELD OF THE INVENTION

This invention relates to methods of preserving the integrity of peptides in the gut. In particular, it concerns the new use of certain compounds as inhibitors of gut proteases.

BACKGROUND ART

The following discussion of the background art is intended to facilitate an understanding of the present invention only. The discussion is not an acknowledgement or admission that any of the material referred to is or was part of the common general knowledge as at the priority date of the application.

Peptides, and in particular polypeptides such as proteins, are increasingly becoming recognised as desirable agents for the treatment of diseases manifesting in the gut (gastrointestinal tract). Protein therapeutics are often based on natural products with a long history of medicinal use, which have a higher safety profile than small molecules that have been newly synthesised and whose effects on the body are largely unknown. Also, proteins can exhibit a high degree of specificity and selectivity, and at the same time can be designed to take advantage of their large size to display multi-functionality, enabling them to interact concurrently with two or more different targets.

Proteins with antioxidant activity, such as superoxide dismutase, are examples of such therapeutic applications. Other examples are monoclonal antibodies, which can act as anti-infectives by binding to sites on infectious organisms invading the gut. Alternatively, such antibodies can bind to receptor sites on intestinal cells, and interfere with adhesion processes and the colonisation of infectious organisms. In addition, these antibodies can interact with cells of the immune system to stimulate their activity in combating infectious diseases. Other types of therapeutic peptides include peptide hormones, such as appetite suppressing agents.

One important drawback to the use of peptides in the intestine is their extreme sensitivity to gut proteases. These proteases can be found both in the stomach (e.g. pepsin), and in the upper intestine, and have evolved to enable the digestive tract to break down peptides ingested as food, by proteolysis, into amino acids which can be taken up as nutrients by receptor-mediated mechanisms.

If the intended site of action of a therapeutic or prophylactic peptide is the small intestine, then the peptide can be protected from breakdown in the stomach by placing it inside an enteric-coated capsule, tablet or other device which resists dissolution at the low pH found in the stomach, but disintegrates at higher pH to release the peptide into the small intestine, e.g. the duodenum, jejunum or ileum. However, the action of the proteases found in the small intestine (in particular the serine proteases, trypsin, chymotrypsin, elastase and carboxypeptidase) is such that they can rapidly break down and destroy peptides once they have been released from such a device. This clearly limits the efficacy of orally administered therapeutic peptides, and a means of preventing their degradation by proteases would markedly enhance their performance.

Although there are many agents acting as protease inhibitors that are known to those skilled in the art, few, if any, are appropriate for this particular application. Most known inhibitors, e.g. antipain, leupeptin, are used for research purposes only, and are not acceptable for human administration. Some inhibitors, e.g diisopropyl fluorophosphate or phenylmethyl sulphonyl fluoride have a high degree of potency, but display a very broad specificity, so there is a risk of their exerting their action in undesirable parts of the body, in addition to the gut. On the other hand, other inhibitors, such as the new class of protease inhibitors employed in the treatment of HIV, are so selective in the nature of the proteases they inhibit that they have no effect on serine proteases in the gut. Two serine protease inhibitors that have been administered to humans are aprotinin and soybean trypsin inhibitor. However; these are relatively expensive to synthesise, and would have to be included in a medicament at such high levels that the cost of the final product would prohibit the manufacture of a medicament for routine daily use.

The present invention seeks to address or at least ameliorate one or more the problems associated with prior art devices.

DESCRIPTION OF THE INVENTION

The inventors have discovered that certain compounds, whose interaction with gut proteases has never previously been recognised, surprisingly, inhibit gut proteases. This enables one to use them to protect peptides from proteolysis (i.e. degradation by gut proteases). The compounds identified as having this activity are biguanides, certain bile acids and pharmaceutically acceptable salts of these compounds.

Accordingly, the present invention provides a compound for use as an inhibitor of one or more gut proteases, which compound is a bile acid, a biguanide or a pharmaceutically acceptable salt of a bile acid or biguanide, wherein said bile acid is of formula (I)

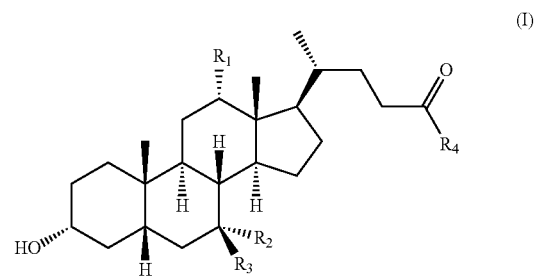

wherein $R^1$, $R^2$ and $R^3$ are each chosen from —H and —OH and $R^4$ is chosen from —OH and —NHCH$_2$CO$_2$H, wherein if $R^1$ and $R^2$ are OH and $R^3$ is H, then $R^4$ must be —NHCH$_2$CO$_2$H.

The mechanism by which the compounds of the invention inhibit gut proteases is structure-specific, presumably the result of a direct binding interaction between the compounds and receptor sites on the proteases. Evidence for this is the fact that other bile acids such as cholic acid, taurocholic acid and taurodeoxycholic acid do not have this inhibitory effect (see FIGS. 5 and 6). Thus, although the inhibitory effect manifests itself at relatively high concentrations of the bile acid, biguanide or derivative thereof, one can rule out non-specific routes of inhibition based on e.g. surfactant interactions or a change in pH. Under the appropriate conditions, the inhibition of protease activity can be 100%.

Inhibitory activity can be demonstrated using fluorogenic or chromogenic peptide substrates. Inhibitory effects have been observed with a range of different peptide substrates, indicating that the effect is not the result of a specific interaction between the peptide substrate and the inhibitor.

As noted above, the compounds of the present invention are for use as inhibitors of one or more gut proteases. Typically they inhibit all gut proteases, i.e. they are for use in inhibiting gut proteases in general. The term "gut proteases" refers to those proteases found in the gut. In this context, and in all other contexts where the word "gut" is used in this specification, it means gastrointestinal tract, and preferably it means the small intestine, such as the duodenum, jejunum or ileum.

Thus, preferably the gut proteases are small intestine proteases, i.e. proteases found in the small intestine. Preferably, the proteases are serine proteases. Said serine proteases may be chosen from trypsin, chymotrypsin, elastase, carboxypeptidase and combinations, thereof. Typically, the compound of the present invention is for use in inhibiting the proteolysis of a peptide, typically in the gut, by said one or more gut proteases.

When the compound of the present invention is a bile acid of formula (I) or a pharmaceutically acceptable salt thereof, preferably at least one of $R^2$ and $R^3$ is —H. It is also preferred that at least one of $R^1$, $R^2$ and $R^3$ is —OH. It is also preferred that no more than two of $R^1$ to $R^4$ are —OH. Typically the compound of the present invention is a bile acid of formula (I) wherein at least one of $R^2$ and $R^3$ is —H,
at least one of $R^1$, $R^2$ and $R^3$ is —OH, and
no more than two of $R^1$ to $R^4$ are —OH, or a pharmaceutically acceptable salt thereof. More preferably it is a bile acid or salt chosen from chenodeoxycholic acid, deoxycholic acid, ursodeoxycholic acid, glycochenodeoxycholic, acid, glycodeoxycholic acid, glycocholic acid and their pharmaceutically, acceptable salts. More preferably it is chosen from chenodeoxycholic acid, deoxycholic acid and their pharmaceutically acceptable salts. Most preferably, it is chenodeoxycholate or a pharmaceutically acceptable salt thereof.

When pharmaceutically acceptable salts of bile acids are referred to, any appropriate pharmaceutically acceptable positively charged ion can be used. Typically an alkali metal such as sodium or potassium is used. Alternative counterions may be used, e.g. an ammonium ion, though this is less preferred. When the compound of the present invention is a bile acid or pharmaceutically acceptable salt thereof, the salt is usually used in preference to the acid, though the same anionic species is formed in the gut in either case; whether the salt or its conjugate acid is present depends on the pH of the medium.

When the compound of the present invention is a biguanide or a pharmaceutically acceptable salt thereof, preferably the biguanide is of formula:

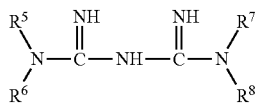

wherein $R^5$, $R^6$, $R^7$ and $R^8$ are each independently chosen from hydrogen, optionally substituted alkyl, optionally substituted phenyl, ethylene glycol, diethylene glycol, triethylene glycol and tetraethylene glycol, except that one of $R^5$, $R^6$, $R^7$ and $R^8$ may be

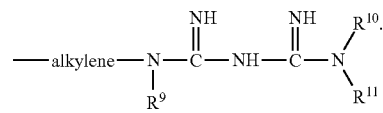

wherein $R^9$, $R^{10}$ and $R^{11}$ are each independently chosen from hydrogen, optionally substituted alkyl, optionally substituted phenyl, ethylene glycol, diethylene glycol, triethylene glycol and tetraethylene glycol.

Preferably, when the optionally substituted alkyl and phenyl groups are substituted, 1 to 3 substituents are present and the substituents are chosen from halo, hydroxy and amino. The alkyl and alkylene groups may be saturated or unsaturated, straight chain or branched, and preferably have from 1 to 6 carbons. The alkylene groups are typically saturated, and are also typically straight chain. Most preferably in this embodiment the biguanide is metformin, phenformin or chlorhexidine or pharmaceutically acceptable salts thereof. The pharmaceutically acceptable salts are suitably the chloride, bromide, iodide or salts of organic acids such as the acetate, propionate, mesylate (methyl sulphonate) or glucuronate.

The ability of the compounds of the invention to inhibit gut proteases, and in particular their ability to inhibit the proteolysis of peptides by gut proteases, makes them particularly useful for co-administration with peptides with prophylactic or therapeutic activity against a disease or condition where the target site for the peptide is the gut, e.g. a disease or condition of the gut or which manifests itself in the gut. In this aspect of the invention the compounds of the present invention may be combined with the peptide prior to administration, in a pharmaceutical composition. Alternatively, the compounds of the present invention may be administered separately to the peptide, the proteolysis of which is to be inhibited, as long as both of them are at some point present in the gut such that the inhibition of proteolysis has a protective benefit for the peptide.

The present invention also provides a method of inhibiting one or more gut proteases, which is typically a method of inhibiting the proteolysis of a peptide (typically in the gut) by one or more gut proteases, which method comprises administering to a subject a compound of the present invention or a pharmaceutical composition of the present invention.

Generally, the present invention is concerned with the treatment of humans, e.g. where "gut" is mentioned it typically refers to the human gut, although in one aspect the invention concerns the treatment of non-human animals. Accordingly the subject in whom the present invention may find specific utility includes, by way of illustration: humans, mammals, companion animals and birds.

Accordingly, the present invention also provides a product containing (a) a compound of the present invention as defined herein; and (b) a peptide, wherein (a) and (b) are prepared for simultaneous, separate or sequential use in the treatment or prevention of a disease or condition, typically a disease or condition of the gut.

In one aspect, the present invention provides a pharmaceutical composition comprising a compound of the present invention together with a peptide (the proteolysis of which is to be inhibited by the compound of the present invention). Typically in this embodiment, the concentration of the compound of the present invention in the composition is at least 20 mg/ml. Generally, it is 100 mg/ml or less. The concentration of the peptide obviously depends on the nature and intended effect of the peptide and the age, size and medical background of the patient.

When the compound of the present invention as defined above is a bile acid or a pharmaceutically acceptable salt thereof, its concentration in the composition is preferably 20-100 mg/ml. Further, the bile acid or pharmaceutically acceptable salt thereof may be present in the composition in an amount of at least 50% by weight, preferably from 60 to 95% and more preferably from 80 to 90%.

Another aspect of the invention provides a pharmaceutical composition comprising:
(i) a peptide or polypeptide; and
(ii) a compound chosen from ursodeoxycholic acid, glycochenodeoxycholate, glycodeoxycholate, glycocholate and their pharmaceutically acceptable salts,
wherein said compound is present in the composition at a concentration of 20 to 100 mg/ml. Although the bile acids and their derivatives in component (ii) are known, they have not previously been used at the high concentrations.

In yet another form, the invention resides in the use of: (i) a peptide or polypeptide; and (ii) a bile salt or pharmaceutically acceptable salt thereof, in the manufacture of a medicament, wherein said bile salt or pharmaceutically acceptable salt thereof is present in the composition at a concentration of 20 to 100 mg/ml and the composition is formulated for delivery through the intestinal tract.

In this form of the invention the bile salt is preferably one or more of ursodeoxycholic acid, glycochenodeoxycholate, glycodeoxycholate, glycocholate and their pharmaceutically acceptable salts.

When the compound of the present invention as defined above is a biguanide or a pharmaceutically acceptable salt thereof, its concentration is preferably 20-100 mg/ml. Further, the biguanide or pharmaceutically acceptable salt thereof may be present in the composition in an amount of at least 50% by weight, preferably from 60 to 95% and more preferably from 80 to 90%.

Another aspect of the invention provides a pharmaceutical composition comprising:
(i) a peptide or polypeptide; and
(ii) a compound chosen from metformin, phenformin in or chlorhexidine or pharmaceutically acceptable salts thereof,
wherein said compound is present in the composition at a concentration of 20 to 100 mg/ml.

In yet another form, the invention resides in the use of: (I) a peptide or polypeptide; and (ii) a biguanide or pharmaceutically acceptable salt thereof, in the manufacture of a medicament, wherein said biguanide or pharmaceutically acceptable salt thereof is present in the composition at a concentration of 20 to 100 mg/ml and the composition is formulated for delivery through the intestinal tract.

In this form of the invention the biguanide is preferably one or more of metformin, phenformin or chlorhexidine or pharmaceutically acceptable salts thereof.

Usually, the pharmaceutical composition of the present invention is suitable for oral administration. In this embodiment, to successfully use a compound of the invention to protect a peptide against degradation by intestinal proteases, it is desirable for the compound of the invention to be co-administered together with the peptide within a vehicle that allows passage across the stomach intact. Such a vehicle may be a tablet, capsule, or pellet, coated, if necessary, with an enteric film that resists dissolution under those conditions found in the stomach, but which is able to break down and release its contents in the small intestine. Where the invention is formulated as tablets, they can be uncoated or coated by known techniques to delay disintegration and absorption in the intestinal tract and thereby provide a sustained action over a longer period. For example, a time delay material such as glyceryl monostearate or glyceryl distearate may be employed.

Pharmaceutical compositions of the present invention that are suitable for oral administration are preferably coated with an enteric coating which becomes permeable at a pH of from 3 to 7. More preferably the coating becomes permeable at a pH of 4 to 6.5 and most preferably 5 to 6. Suitable enteric coatings are known in the art. The compounds of the present invention are typically formulated with such an enteric coating.

A pharmaceutical composition of the present invention may comprise other standard pharmaceutical excipients in admixture, to provide a composition in the form of a powder, a liquid, a gel, a paste, a wax or a suspension. For instance, pharmaceutical excipients capable of enhancing dissolution of the compound of the invention or the peptide, or which act as anti-oxidants, preservatives, glidants (for example magnesium stearate, stearic acid or talc), swelling agents, disintegrants (for example, corn starch, or alginic acid), binding agents, (for example starch, gelatin or acacia) etc may also be included in pharmaceutical compositions of the present invention.

As used herein, the term peptide refers to an amide obtainable from two or more amino carboxylic acid molecules, which may be the same or different, by formation of a covalent bond from the carbonyl carbon of one to the nitrogen atom of another with formal loss of water. The amino acid molecules can be of the D- or L-form. Typically, the peptides are obtainable from α-amino acids, but they may also be obtainable from non α-amino acids or a mixture of α- and non α-amino acids. Preferably, the peptides are obtainable from natural amino acids. In one aspect the amino acids are obtainable or obtained by chemically modifying natural amino acids after the peptide has been synthesized.

In one embodiment the peptides are polypeptides, i.e. peptides with 10 or more amino acid residues. In a preferred aspect of this embodiment the polypeptide is a protein. In another embodiment the peptide has 2 to 9 amino acid residues.

Illustrative peptides and polypeptides that have particular application to the invention include such molecules as insulin; calcitonin; human serum albumin; growth hormone; growth hormone releasing factors; galanin; parathyroid hormone; peptide YY; oxyntomodulin; blood clotting proteins such as kinogen, prothombin, fibrinogen, Factor VII, Factor VIII of Factor IX; erythropoietins and EPO mimetics; colony stimulating factors including GCSF and GMCSF; platelet-derived growth factors; epidermal growth factors; fibroblast growth factors; transforming growth factors; GLP-1, GLP-2; exendin; leptin; GAG; cytokines; insulin-like growth factors; bone- and cartilage-inducing factors; neurotrophic factors; interleukins including IL-1, IL-2, IL-3, IL-4, IL-5, IL-6, IL-7, IL-8, IL-9, IL-10, IL-11, IL-12; interferons including interferon gamma, interferon-1a, interferon alphas; TNF alpha; TNF beta; TGF-beta; cholera toxin A and B fragments; *E. coli* enterotoxin A and B fragments; secretin; enzymes including histone deacetylase, superoxide dismutase, catalase, adenosine deaminase, thymidine kinase, cytosine deaminase, proteases, lipases, carbohydrases, nucleotidases, polymerases, kinases and phosphatases; transport or binding proteins especially those which bind and/or transport a vitamin, metal ion, amino acid, or lipid or lipoprotein such as cholesterol ester transfer protein, phospholipid transfer protein, HDL binding protein; connective tissue proteins such as a collagen, elastin or fibronectin; a muscle protein such as actin, myosin, dystrophin, or mini-dystrophin; a neuronal, liver, cardiac, or adipocyte protein; a cytotoxic protein; a cytochrome; a protein which is able to cause replication, growth or differentiation of cells; a signalling molecule such as an intra-cellular signalling protein or an extracellular signalling protein (eg hormone); trophic factors such as BDNF, CNTF5NGF, IGF, GMF, aFGF, bFGF, VEGF, NT3, T3 and HARP; apolipoproteins; antibody molecules; receptors in soluble form such as T-cell receptors and receptors for cytokines, interferons or chemokines; proteins or peptides containing antigenic epitopes and fragments; and derivatives, conjugates and sequence variants of any of the above. These and other proteins may be derived from human, plant, animal, bacterial or fungal sources, and extracted either from natural sources, prepared as recombinants by fermentation or chemically synthesised As the compounds of the present, invention inhibit proteolysis, which involves the breaking down of peptide bonds, they may be used to inhibit the proteolysis of any peptide. Preferably the peptide is one that is capable of having a beneficial effect when placed in the gut. The beneficial effect may be, for example, therapeutic, cosmetic or preventative such as prophylactic or contraceptive. The peptide can be of natural (biological), synthetic or semi-synthetic, origin.

Typically the peptide is for use in the prophylaxis or treatment of a disease or condition of the gut, or which manifests itself in the gut. Thus, the peptide could be for use in the treatment of Crohn's disease, or an infection of the gut or part of the gut, e.g. it could be a peptidic antibiotic. In one aspect the peptide could be a cyclic peptide. Such cyclic peptides could be used in cancer or inflammatory diseases of the intestine such as Crohn's, disease, inflammatory bowel disease and the like. As will be appreciated though, the present invention works with all peptides so there is no limit on the type of peptide to be used.

Cyclic peptides are known in the art to have a conformation which is more constrained than linear peptides. The freedom of movement of the ends of the peptide is limited in a cyclic peptide because they have been anchored together chemically. In a form of the invention, the peptide employed in the invention is a cyclic peptide having a ring of at least six amino acids, wherein the ring comprises a plurality of amino acid domains, wherein each domain comprising at least two epitope-forming amino acids, and two or more associating functional groups. The amino acids employed in the cyclic peptide can be any of the natural amino acids, substituted derivatives, analogues, and L or D forms thereof.

Cyclic peptides of the type are described in detail in patent specification PCT/GB2007/003592 are preferably selected for use in this invention. The content and specific disclosure in patent specification PCT/GB2007/003592 is incorporated herein by reference.

Pharmaceutical compositions of the present invention may be made by preparation of a substantially anhydrous mixture containing the peptide and the compound of the present invention. Depending on the desired formulation of the composition it may then be appropriate to fill uncoated capsules with the mixture and then coat the capsules with an appropriate polymer mixture to achieve particular permeability properties. Depending on the nature of additional excipients employed, the pharmaceutical composition of the invention may be in liquid, solid, semi-solid or gel form.

General

Those skilled in the art will appreciate that the invention described herein is susceptible to variations and modifications other than those specifically described. The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the description of the invention and apply throughout. Unless otherwise defined, all other technical terms used herein have the same meaning as commonly understood to one of ordinary skill in the art to which the invention belongs.

BRIEF DESCRIPTION OF THE DRAWINGS

Aspects of the invention will now be described, by way of example only, with reference to the following description and figures.

ILLUSTRATIVE EMBODIMENTS OF THE INVENTION

The following Examples serve to illustrate the present invention, and should not be construed as limiting. In Examples 1-9, 12 and 13 the progress of the enzymatic reaction was assessed by measuring the appearance of reaction product (amino-4methyl coumarin) fluorimetrically using an excitation wavelength of 365 nm, and an emission wavelength of 440 nm (cut-off 435 nm) on a Spectramax Gemini XS machine from Molecular Devices.

Example 1

Figure 1:
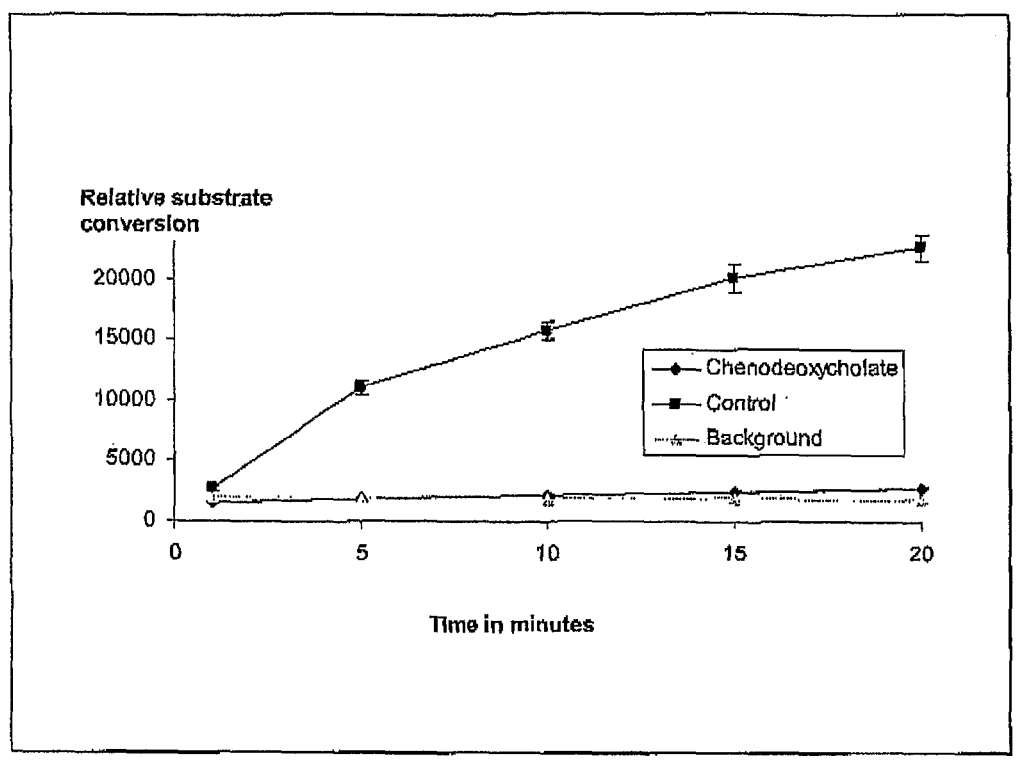
FIG. 1 illustrates the inhibition of trypsin by chenodeoxycholate in a time course reaction where the peptide substrate is Z-L-Arg 7-amido-4-methylcoumarin HCl-Chenodeoxycholate at 100 mg/ml.
Figure 2:
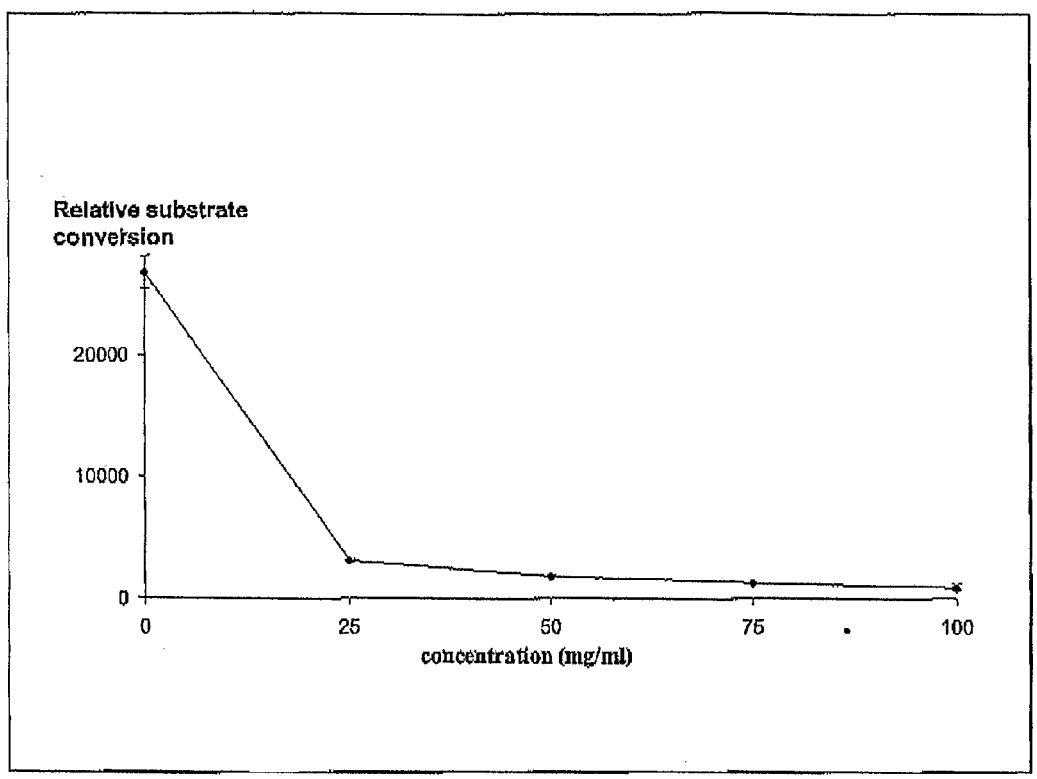
FIG. 2 illustrates inhibition of trypsin activity by chenodeoxycholate. A dose-response curve is presented for the peptide substrate —Z-L-Arg 7-amido-4-methylcoumarin HCl, wherein the incubation time is 20 minutes.

Trypsin, from bovine pancreas, was dissolved in Hanks Balanced Salt Solution (HBSS) at a concentration of 0.02 mg/ml. The substrate Z-L-arginine 4-methyl-7coumarinylamide was dissolved in HBSS at a concentration of 0.01 mg/ml, and sodium chenodeoxycholate was dissolved at a range of concentrations starting at 100 mg/ml. The assay was conducted in the wells of 96-well black plastic microplates, in which 20:1 of enzyme solution and 60:1 of bile salt were mixed together, and then 20:1 of substrate was added, with mixing, at the start of the reaction, which proceeded at room temperature for up to 30 minutes, with measurement at various intermediate time points. Inhibition of enzyme activity by chenodeoxycholate over time is shown in FIG. 1, and a dose response curve with chenodeoxycholate at different concentrations is shown in FIG. 2.

Example 2

Example 1 was repeated but with chymotrypsin as the protease (instead of trypsin) and with glutaryl-L-phenylalanine 4-methyl-7-coumarinylamide as the substrate.

Figure 3:
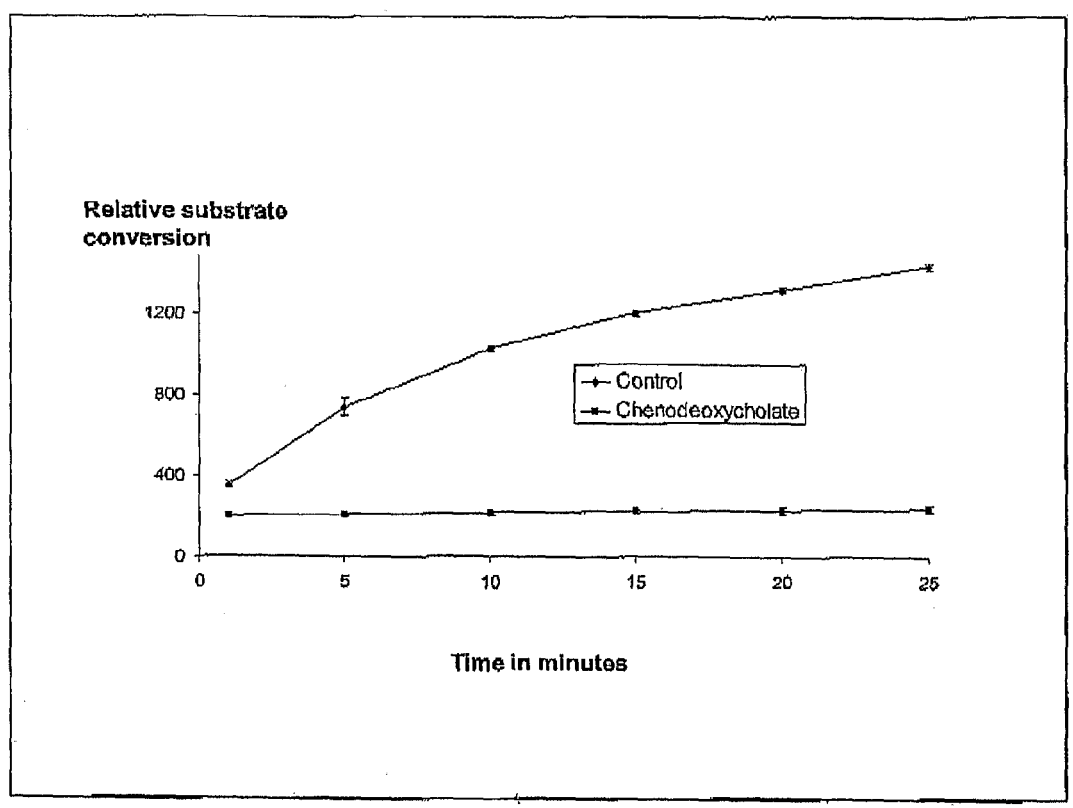
FIG. 3 illustrates the inhibition of chymotrypsin by chenodeoxycholate in a time course reaction where the peptide substrate is glutaryl-L-phenylalanine 4-methyl-7-coumarinylamide chenodeoxycholate at a concentration of 100 mg/ml.
Figure 4:
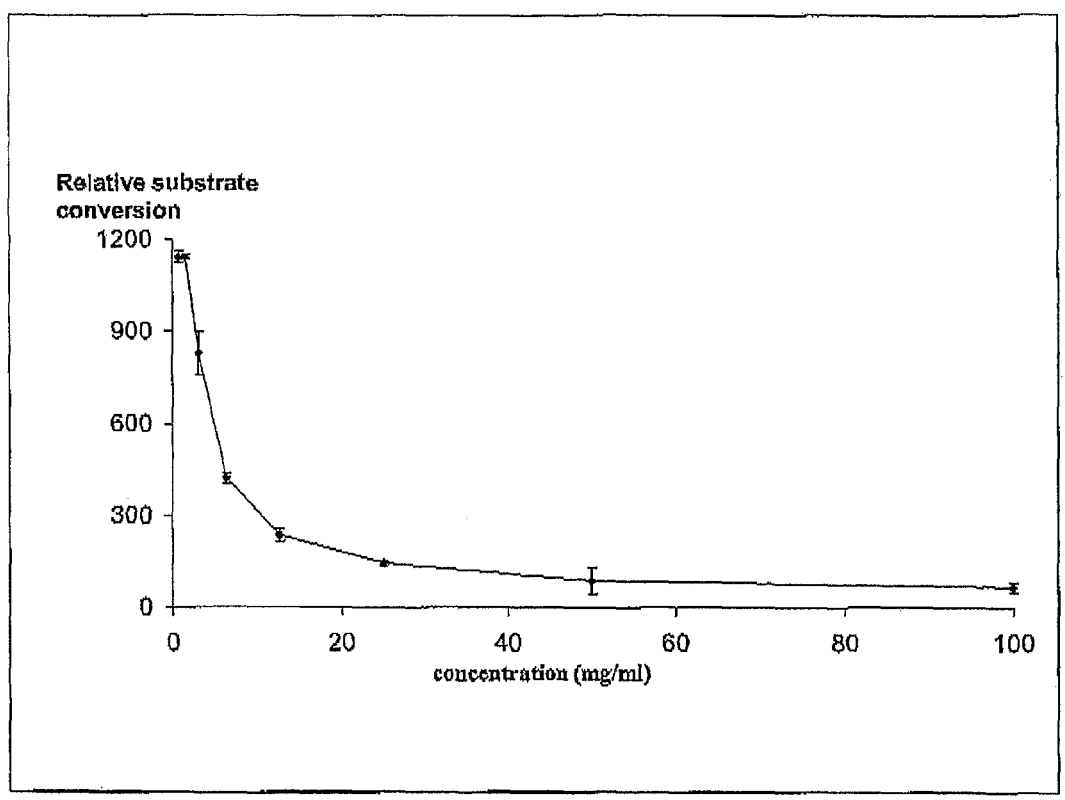
FIG. 4 illustrates inhibition of chymotrypsin activity by chenodeoxycholate. A dose response curve is presented for the peptide substrate -glutaryl-L-phenylalanine 4-methyl-7-coumarinylamide, over an incubation time of 20 minutes.

Inhibition of enzyme activity by chenodeoxycholate over time is shown in FIG. 3, and a dose response curve with chenodeoxycholate at different concentrations is shown in FIG. 4.

Example 3

Figure 5:
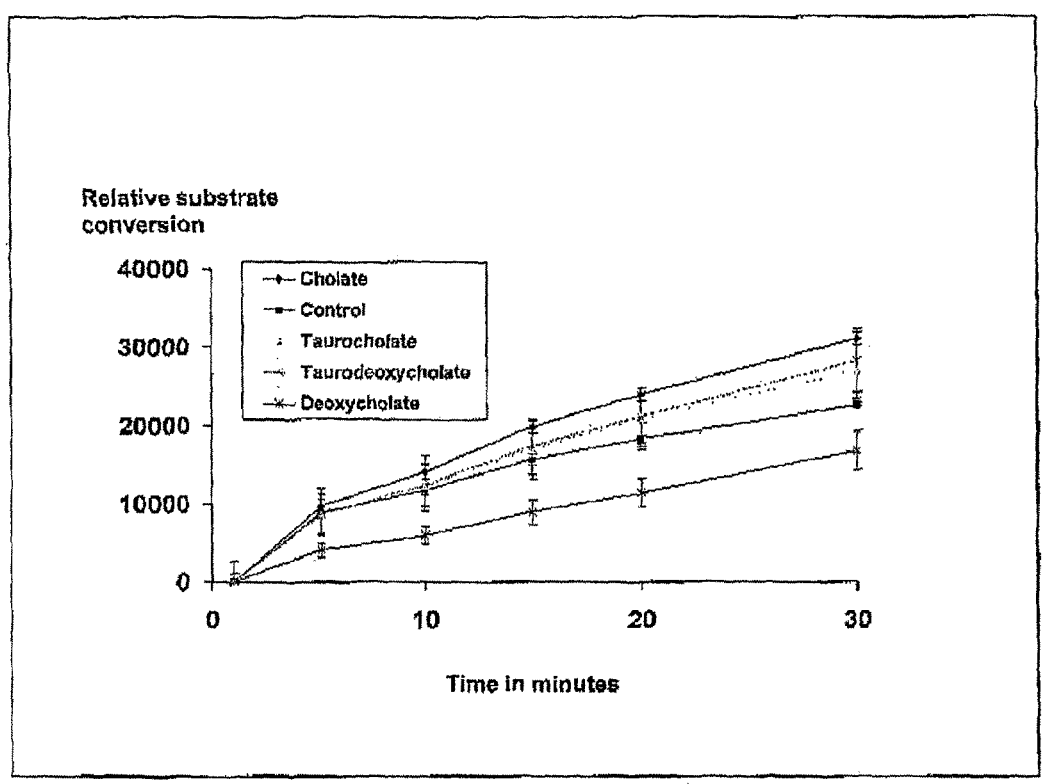
FIG. 5 illustrates inhibition of trypsin by deoxycholate in a time course reaction where the peptide substrate is Z-L-Arg 7-amido-4-methylcoumarin HCl Deoxycholate at a concentration of 25 mg/ml.

Example 1 was repeated but with sodium deoxycholate instead of sodium chenodeoxycholate. Inhibition of enzyme activity by deoxycholate over time is shown in FIG. 5. FIG. 5 also includes results for when cholate, taurocholate and taurodeoxycholate were used instead of deoxycholate, showing that these three compounds do not inhibit trypsin.

Example 4

Figure 6:
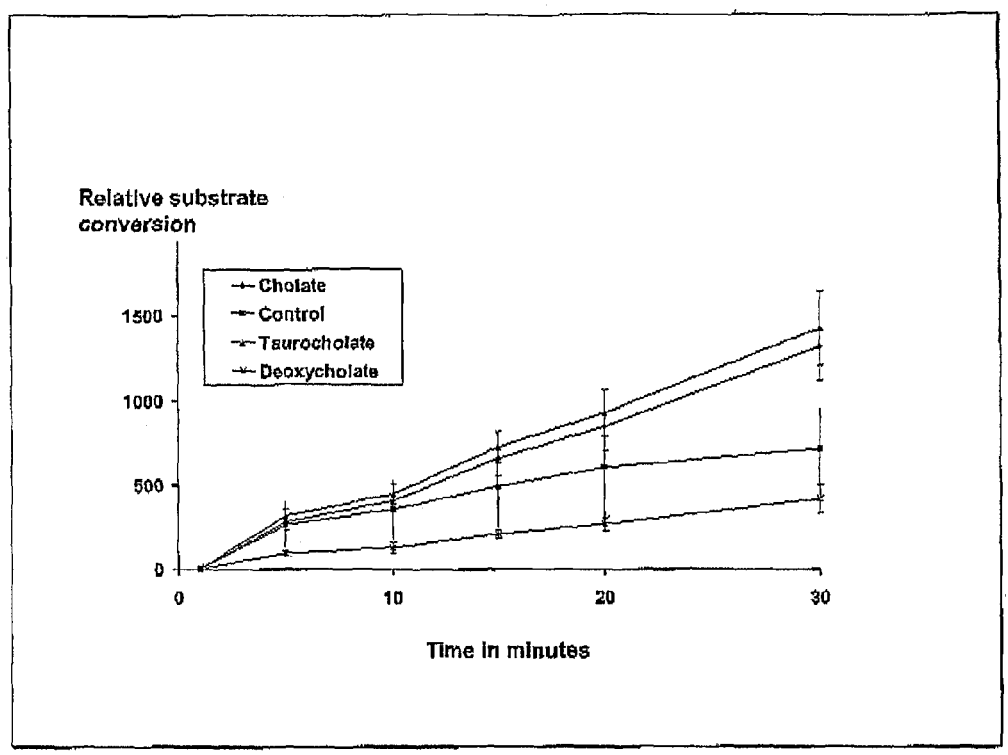
FIG. 6 illustrates inhibition of chymotrypsin by deoxycholate in a time course reaction where the peptide substrate is glutaryl-L-phenylalanine 4-methyl-7-coumarinylamide bile salt at a concentration of 25 mg/ml.

Example 2 was repeated but with sodium deoxycholate instead of sodium chenodeoxycholate. Inhibition of enzyme activity by deoxycholate over time is shown in FIG. 6. FIG. 6 also includes results for when cholate and taurocholate were used instead of deoxycholate, showing that these two compounds do not inhibit chymotrypsin.

Example 5

Figure 7:
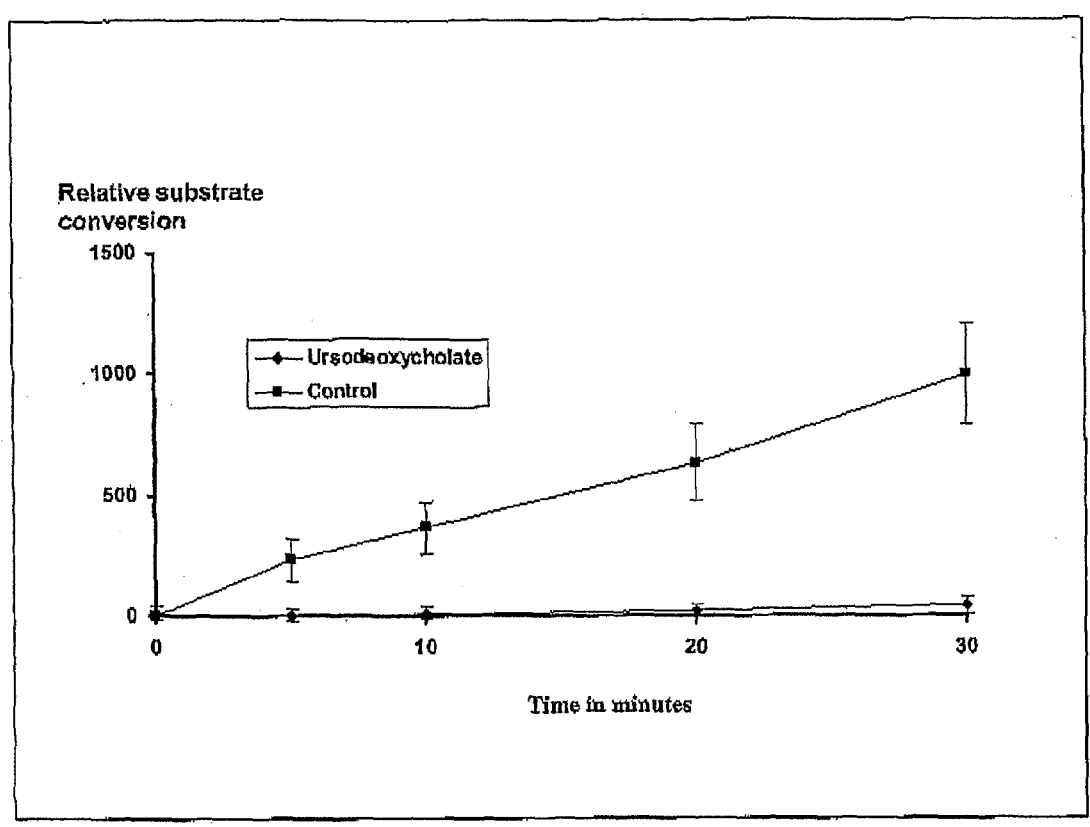
FIG. 7 illustrates inhibition of trypsin activity by ursodeoxycholate in a time course reaction where the peptide substrate is Z-L-Arg 7-amido-4-methylcoumarin HCl Bile salt at a concentration of 25 mg/ml.
Figure 8:
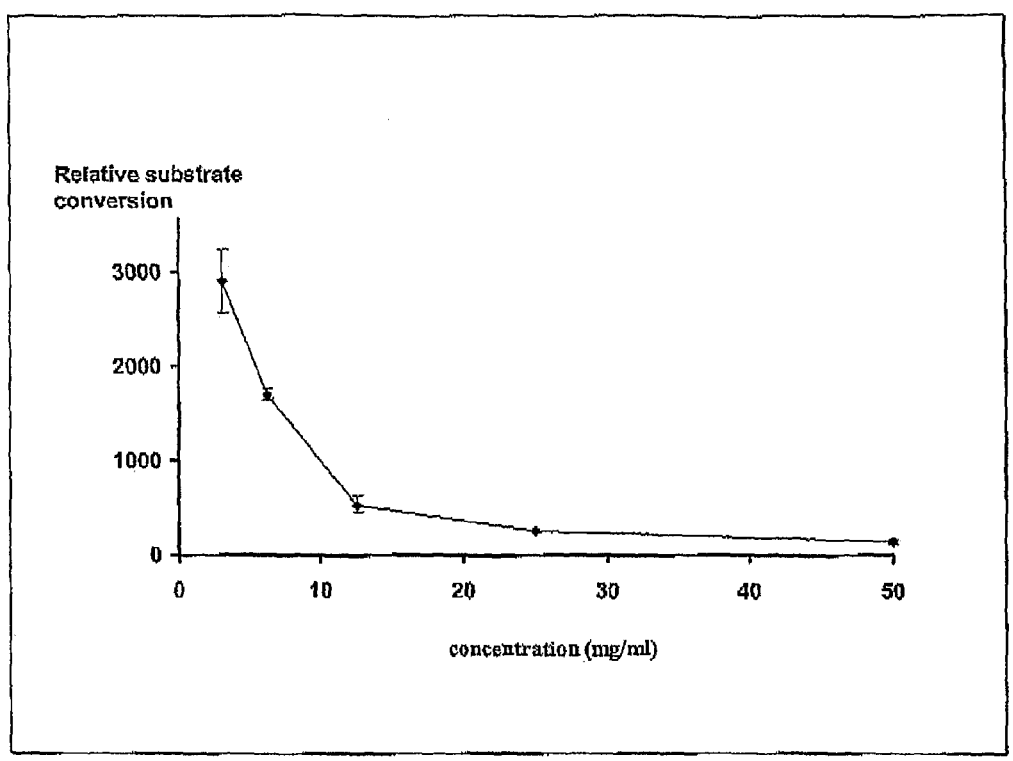
FIG. 8 illustrates inhibition of trypsin activity by ursodeoxycholate. A dose response curve is presented for the peptide substrate Z-L-Arg 7-amido-4-methylcoumarin HCl with an incubation time—20 minutes.

Trypsin, from bovine pancreas, was dissolved in HBSS at a concentration of 0.02 mg/ml. The substrate Z-L-arginine 4-methyl-7-coumarinylamide was dissolved in HBSS at a concentration of 0.01 mg/ml, and sodium ursodeoxycholate was dissolved at a range of concentrations starting at 50 mg/ml. The assay was conducted in the wells of 96-well black plastic microplates, in which 20:1 of enzyme solution and 100:1 of bile salt were mixed together, and then 20:1 of substrate was added, with mixing, at the start of the reaction, which proceeded at 37° C. for up to 30 minutes, with measurement at various intermediate time points. Inhibition of enzyme activity by ursodeoxycholate over time is shown in FIG. 7, and a dose response curve with ursodeoxycholate at different concentrations is shown in FIG. 8.

Example 6

Figure 9:
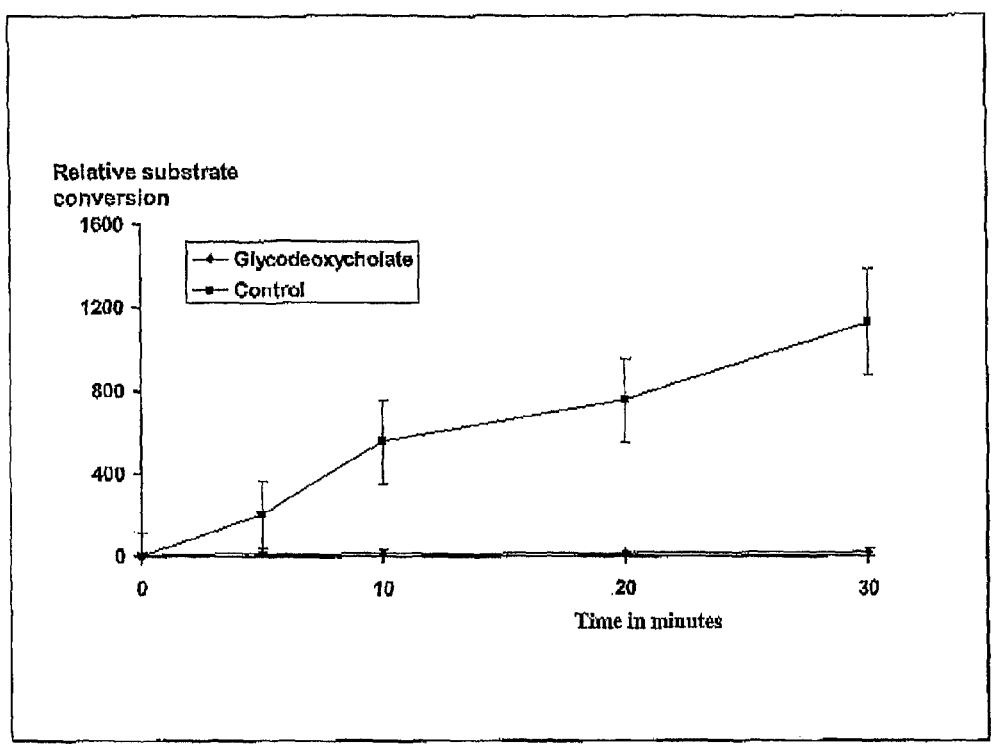
FIG. 9 illustrates inhibition of trypsin activity by glycodeoxycholate in a time course reaction wherein the peptide substrate is Z-L-Arg 7-amido-4-methylcoumarin HCl Bile salt at a concentration of 25 mg/ml.

Trypsin, from bovine pancreas, was dissolved in HBSS at a concentration of 0.02 mg/ml. The substrate Z-L-arginine 4-methyl-7-coumarinylamide was dissolved in HBSS at a concentration of 0.01 mg/ml, and sodium glycodeoxycholate was dissolved at a range of concentrations starting at 100 mg/ml. The assay was conducted in the wells of 96-well black plastic microplates, in which 20:1 of enzyme solution and 100:1 of bile salt were mixed together, and then 20:1 of substrate was added, with mixing, at the start of the reaction, which proceeded at 37° C. for up to 30 minutes, with measurement at various intermediate time points. Inhibition of enzyme activity by glycodeoxycholate over time is shown in FIG. 9.

Example 7

Figure 10:
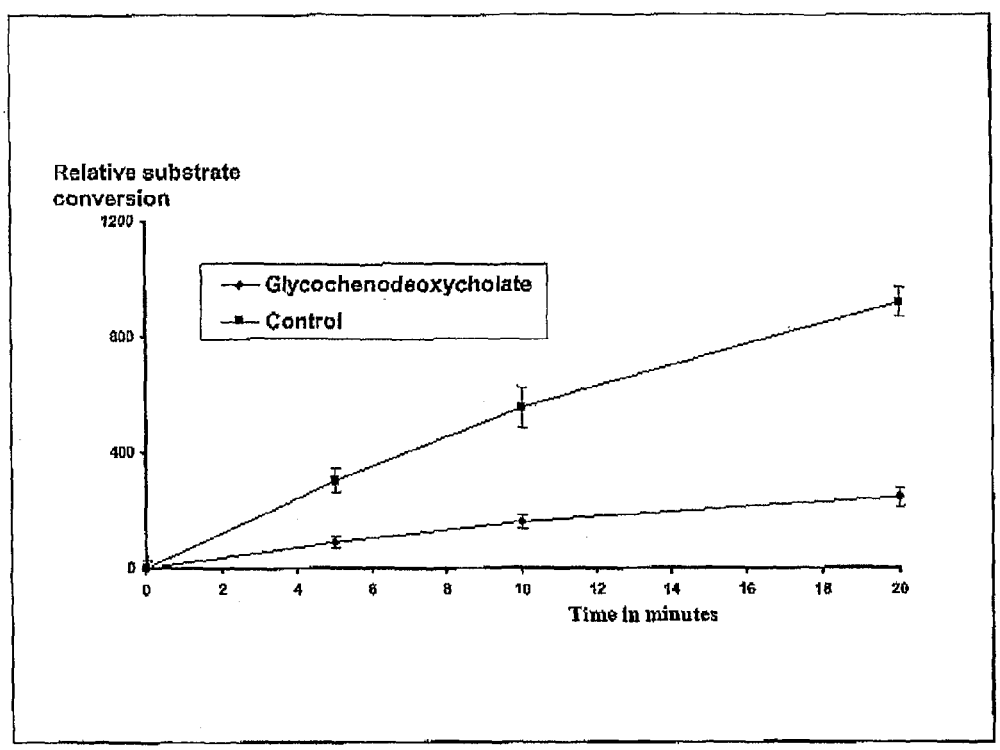
FIG. 10 illustrates inhibition of trypsin activity by glycochenodeoxycholate in a time course reaction where the peptide substrate is Z-L-Arg 7-amido-4-methylcoumarin HCl and the incubation time is 20 minutes.

Example 5 was repeated but with sodium glycochenodeoxycholate instead of sodium ursodeoxycholate. Inhibition of enzyme activity by glycochenodeoxycholate over time is shown in FIG. 10.

Example 8

Figure 11:
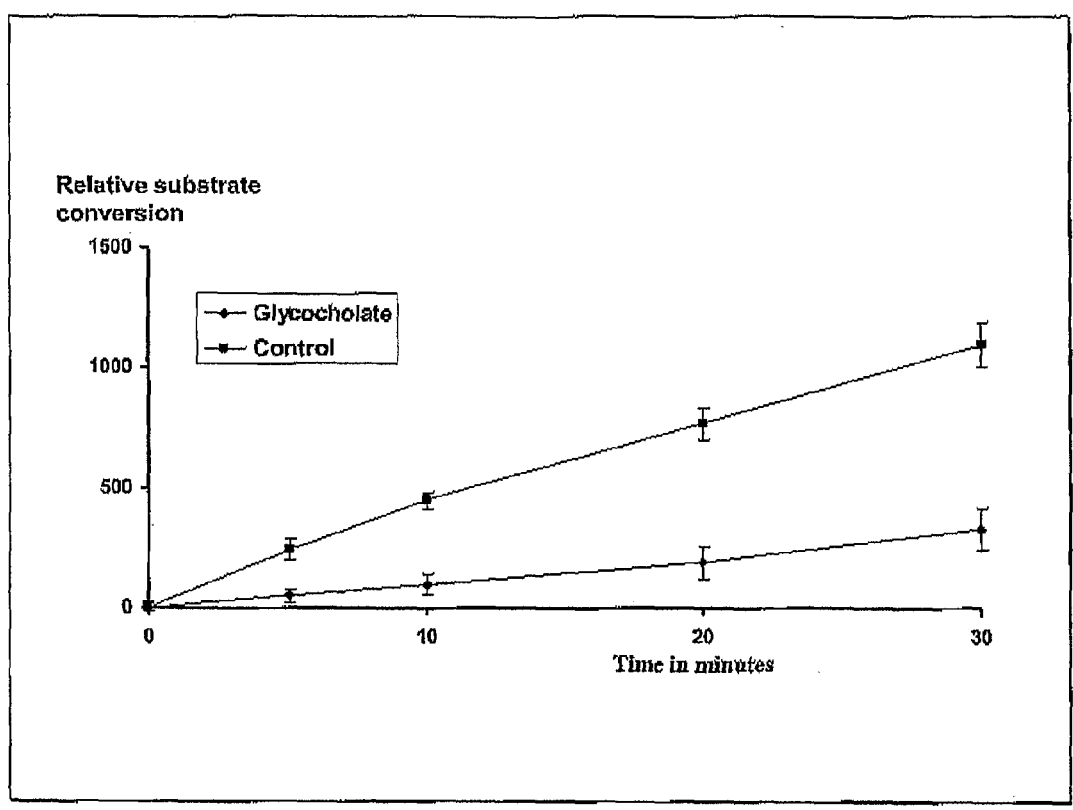
FIG. 11 illustrates inhibition of trypsin activity by glycocholate in a time course reaction where the peptide substrate is Z-L-Arg 7-amido-4-methylcoumarin HCl and the incubation time is 20 minutes.

Example 6 was repeated but with sodium glycocholate instead of sodium glycodeoxycholate. Inhibition of enzyme activity by glycocholate over time is shown in FIG. 11.

Example 9

Figure 12:
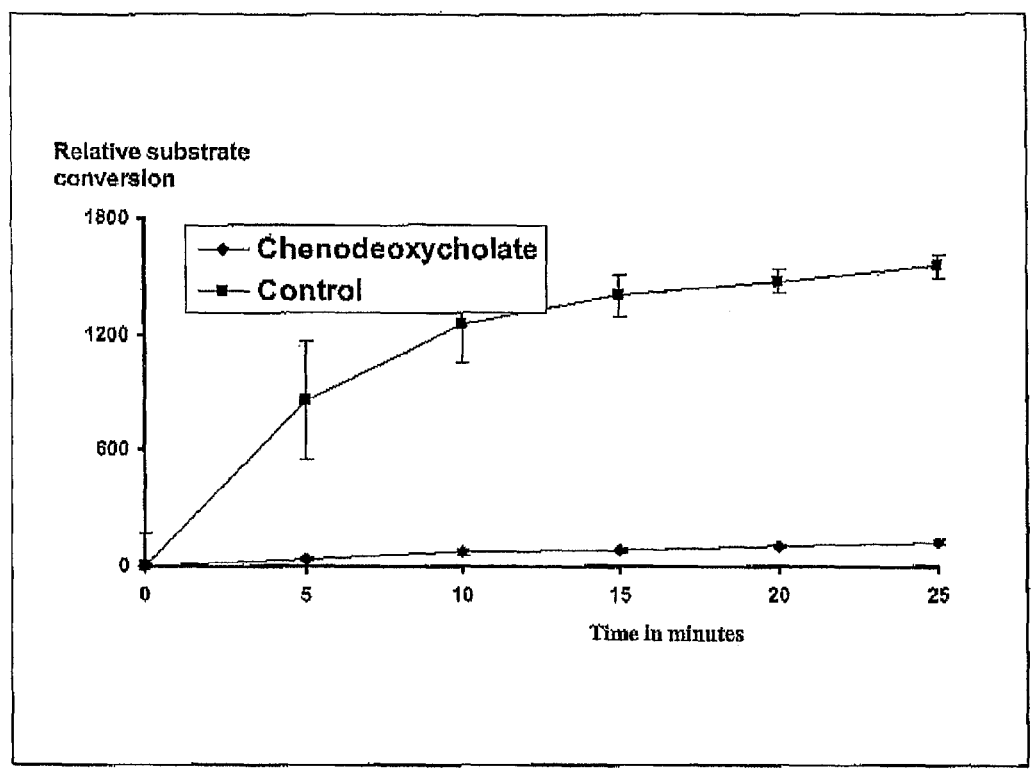
FIG. 12 illustrates inhibition of chymotrypsin activity by chenodeoxycholate in a time course reaction where the peptide substrate is Boc-β-benzyl-Asp-Pro-Arg-7-amido-4-methylcoumarin HCl and the incubation time is 20 minutes.

Chymotrypsin, from bovine plasma, was dissolved in HBSS at a concentration of 0.02 mg/ml. The substrate Boc-β-benzyl-Asp-Pro-Arg-7-amido-4-methylcoumarin was dissolved in HBSS at a concentration of 0.01 mg/ml, and sodium chenodeoxycholate was dissolved at 100 mg/ml. The assay was conducted in the wells of 96-well clear plastic microplates, in which 20:1 of enzyme solution and 60:1 of bile salt were mixed together, and then 20:1 of substrate was added, with mixing, at the start of the reaction, which proceeded at 37° C. for up to 30 minutes, with measurement at various intermediate time points. Inhibition of enzyme activity by chenodeoxycholate over time is shown in FIG. 12.

Example 10

Figure 13:
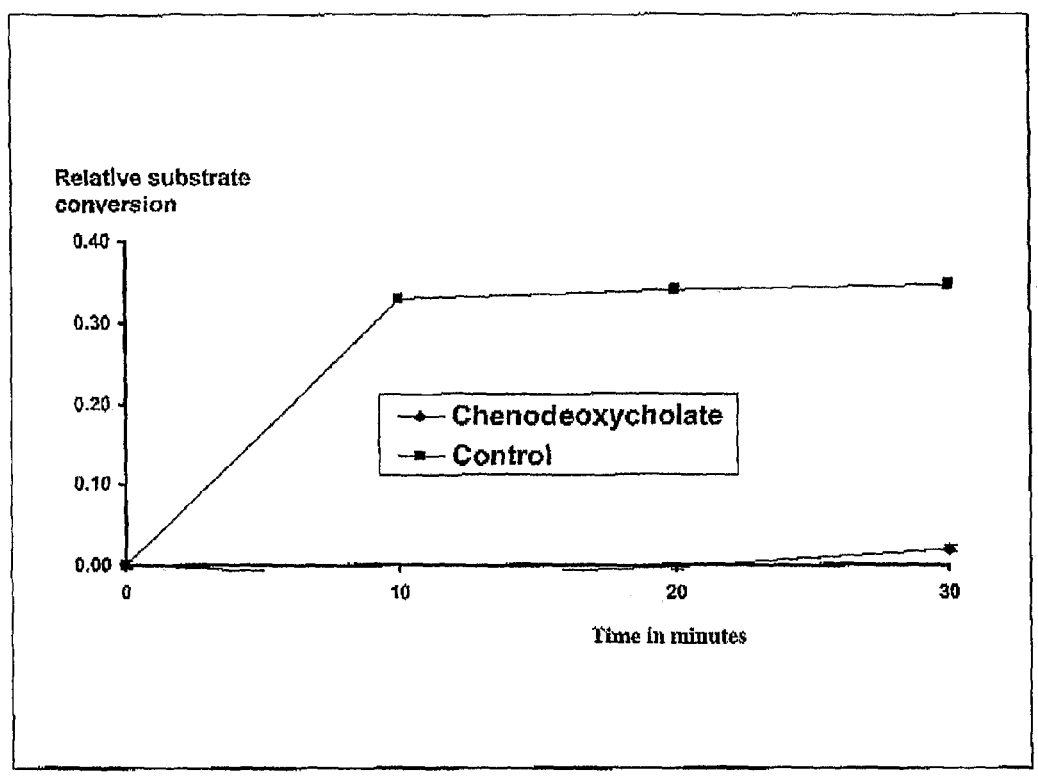
FIG. 13 illustrates inhibition of thrombin activity by chenodeoxycholate in a time course reaction where the peptide substrate is N-Benzoyl-Phe-Val-Arg-p-nitroanilide hydrochloride and the incubation time is 20 minutes.

Thrombin, from bovine plasma, was dissolved in HBSS at a concentration of 0.5 mg/ml. The substrate N-Benzoyl-Phe-Val-Arg-p-nitroanilide hydrochloride was dissolved in HBSS at a concentration of 0.5 mg/ml, and sodium chenodeoxycholate was dissolved at a range of concentrations starting at 100 mg/ml. The assay was conducted in the wells of 96-well clear plastic microplates, in which 50:1 of enzyme solution and 100:1 of bile salt were mixed together, and then 50:1 of substrate was added, with mixing, at the start of the reaction, which proceeded at 37° C. for up to 30 minutes, with measurement at various intermediate time points. The progress of the enzymatic reaction was assessed by measuring the appearance of reaction product (p-nitroaniline) colorimetrically using a wavelength of 405 nm on an Anthos reader 2001 from Anthos Labtec Instruments. Inhibition of enzyme activity by chenodeoxyoholate over time is shown in FIG. 13.

Example 11

Figure 14:
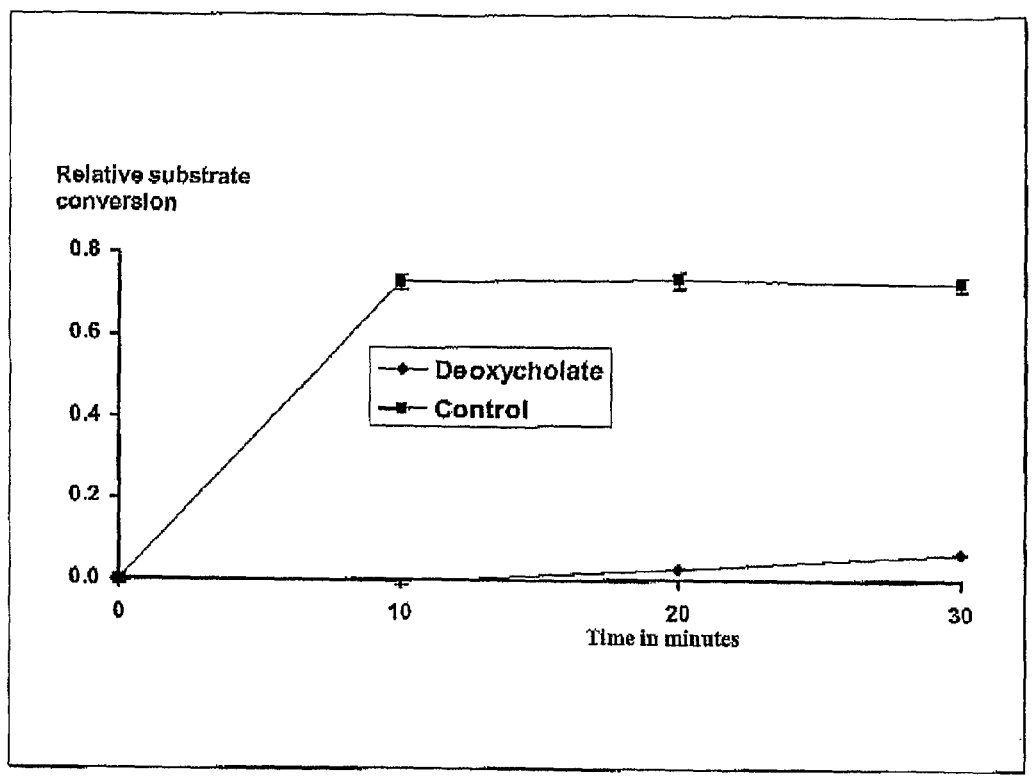
FIG. 14 illustrates inhibition of thrombin activity by deoxycholate in a time-course reaction where the peptide substrate is N-Benzoyl-Phe-Val-Arg-p-nitroanilide hydrochloride and the incubation time is 20 minutes.

Example 10 was repeated but with sodium deoxycholate instead of sodium chenodeoxycholate. Inhibition of enzyme activity by deoxycholate over time is shown in FIG. 14.

Example 12

Figure 15:
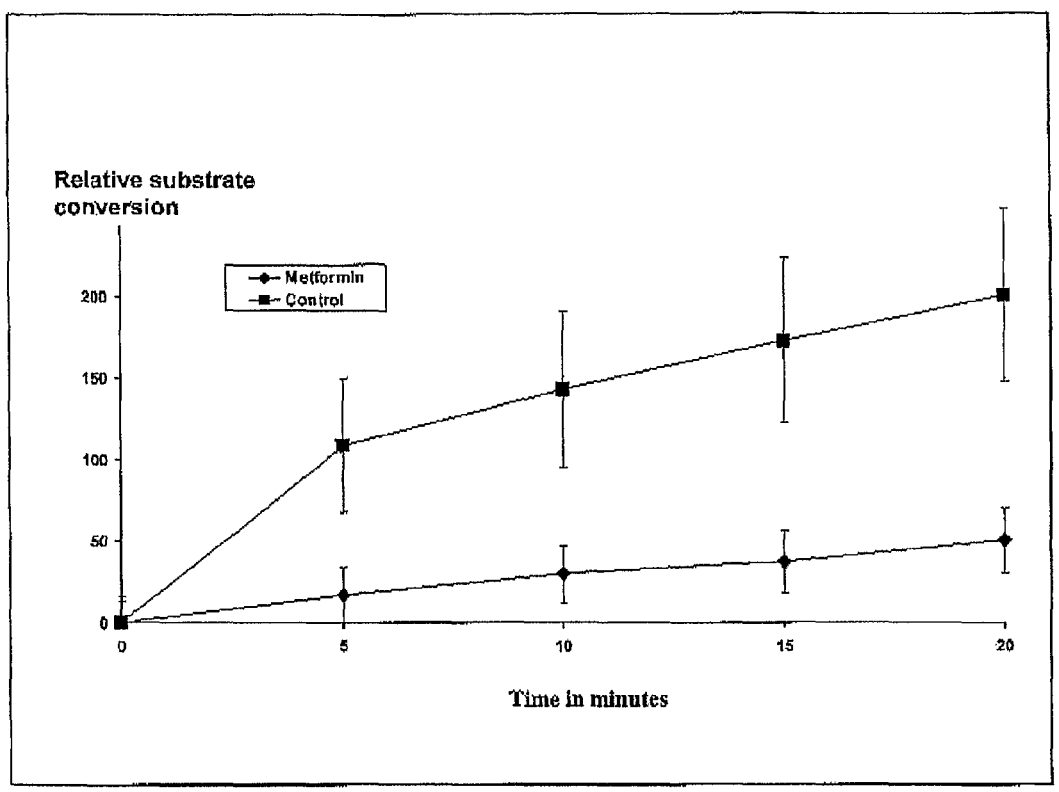
FIG. 15 illustrates the inhibition of trypsin activity by metformin in a time course reaction where the peptide substrate is Z-L-Arg 7-amido-4-methylcoumarin HCl and the incubation time is 20 minutes.

Example 9 was repeated but with trypsin (instead of chymotrypsin) from bovine plasma, Z-L-arginine 4-methyl-7-coumarinylamide as the substrate and metformin as the inhibitor. Inhibition of enzyme activity by metformin over time is shown in FIG. 15.

Example 13

Figure 16:
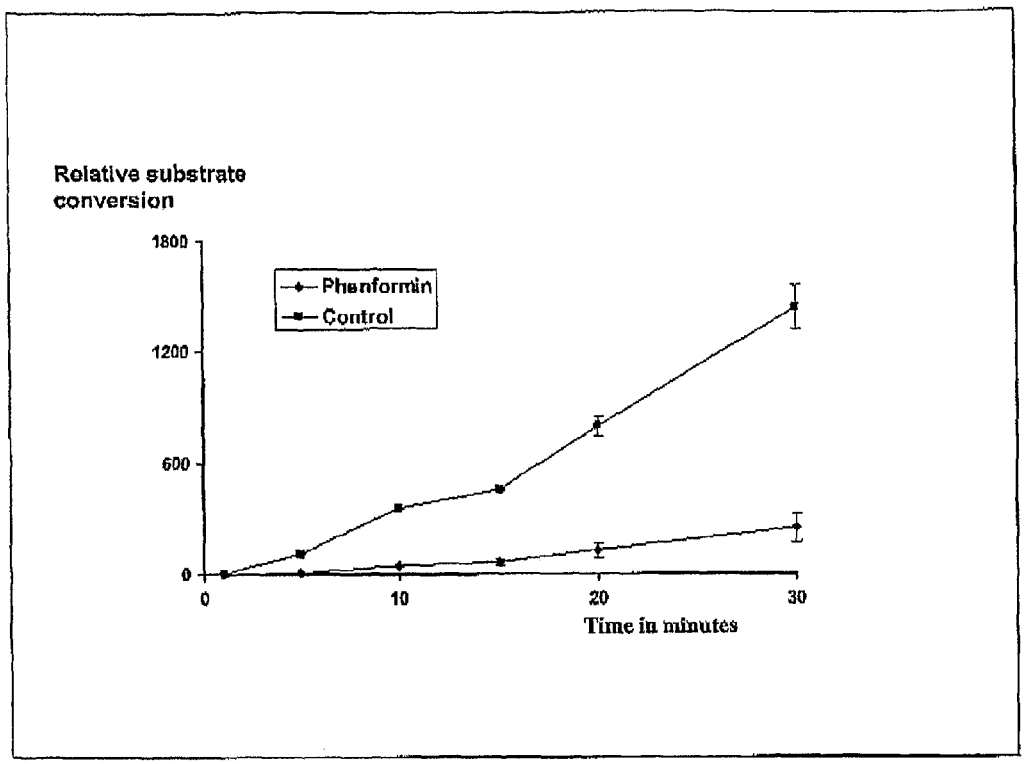
FIG. 16 illustrates inhibition of trypsin activity by phenformin in a time course reaction where the peptide substrate is Z-L-arginine 4-methyl-7-coumarinylamide and the incubation time is 20 minutes.

Trypsin, from bovine pancreas, was dissolved in HBSS at a concentration of 0.02 mg/ml. The substrate Z-L-arginine 4-methyl-7-coumarinylamide was dissolved in HBSS at a concentration of 0.01 mg/ml, and phenformin was dissolved at 100 mg/ml. The assay was conducted in the wells of 96-well black plastic microplates, in which 20:1 of enzyme solution and 100:1 of bile salt were mixed together, and then 20:1 of substrate was added, with mixing, at the start of the reaction, which proceeded at 37° C. for up to 30 minutes, with measurement at various intermediate time points. Inhibition of enzyme activity by phenformin over time is shown in FIG. 16.

Modifications and variations such as would be apparent to a skilled addressee are deemed to be within the scope of the present invention.

The invention claimed is:

1. A composition comprising:
   one or more therapeutic peptide(s) or polypeptide(s), and
   a compound selected from the group consisting of:
      chenodeoxycholic acid,
      ursodeoxycholic acid,
      glycodeoxycholic acid,
      glycochenodeoxycholic acid, and
      a pharmaceutically acceptable salt thereof,
   wherein the compound is active in the small intestine as an inhibitor of gut serine protease(s), and
   wherein the compound is present in the gut at an initial concentration of 20 to 100 mg/ml.

2. A composition for the treatment of a disease or condition affecting the gut of a subject wherein the composition is a composition according to claim 1.

3. The composition according to claim 1, wherein the compound is present in an amount of at least 50% by weight.

4. The composition according to claim 1, wherein the compound is present in an amount of at least 60 to 95%.

5. The composition according to claim 1, wherein the therapeutic peptide is a cyclic peptide.

6. A method comprising the step of:
   administering to a subject a composition comprising a therapeutic peptide(s) or polypeptide(s) and a compound,
   wherein the compound is selected from the group consisting of:
      chenodeoxycholic acid,
      ursodeoxycholic acid,
      glycodeoxycholic acid, and
      pharmaceutically acceptable salts thereof,
   wherein the compound is active in the small intestine as an inhibitor of gut serine protease(s), and inhibits the degradation of the one or more therapeutic peptide(s) or polypeptide(s) by one or more gut serine proteases, and
   wherein the compound is present in the gut in a concentration of 20 to 100 mg/ml.

* * * * *